United States Patent
Fukazawa et al.

(10) Patent No.: US 6,646,735 B2
(45) Date of Patent: Nov. 11, 2003

(54) SURFACE INSPECTION APPARATUS AND SURFACE INSPECTION METHOD

(75) Inventors: Kazuhiko Fukazawa, Misato (JP); Mari Yamamoto, Meguro-ku (JP); Takeo Oomori, Hachioji (JP)

(73) Assignee: Nikon Corporation, Tokyo (JP)

( * ) Notice: Subject to any disclaimer, the term of this patent is extended or adjusted under 35 U.S.C. 154(b) by 138 days.

(21) Appl. No.: 09/949,747

(22) Filed: Sep. 12, 2001

(65) Prior Publication Data

US 2002/0093647 A1 Jul. 18, 2002

(30) Foreign Application Priority Data

Sep. 13, 2000 (JP) .................................. 2000-277804
Sep. 13, 2000 (JP) .................................. 2000-277805
Dec. 5, 2000 (JP) .................................. 2000-369814
Dec. 5, 2000 (JP) .................................. 2000-370695

(51) Int. Cl.$^7$ ............................................... G01N 21/00
(52) U.S. Cl. ............................ 356/237.4; 356/237.2; 356/237.1
(58) Field of Search ........................ 356/237.1, 237.2, 356/237.4, 237.5, 239.7, 239.8

(56) References Cited

U.S. PATENT DOCUMENTS

| 5,777,729 A | 7/1998 | Aiyer et al. |
| 6,097,483 A | 8/2000 | Komatsu |

FOREIGN PATENT DOCUMENTS

| JP | 07-027709 A | 1/1995 |
| JP | 08-075661 A | 3/1996 |
| JP | 10-239038 A | 9/1998 |
| JP | 10-325805 A | 12/1998 |
| JP | 10-339701 A | 12/1998 |
| JP | 11-051874 A | 2/1999 |
| JP | 2000-206050 A | 7/2000 |

OTHER PUBLICATIONS

U.S. patent application Ser. No. 09/083,538, Tanaka, filed May 22, 1998.
U.S. patent application Ser. No. 09/481,503, Komatsu et al., filed Jan. 12, 2000.
U.S. patent application Ser. No. 09/578,711, Oomori et al., filed May 26, 2000.
U.S. patent application Ser. No. 09/836,185, Oomori et al., filed Apr. 18, 2001.
U.S. patent application Ser. No. 09/462,279, Komatsu et al., filed Jul. 09, 1998.
U.S. patent application Ser. No. 09/781,957, Oomori et al. filed Feb. 14, 2001.
U.S. patent application Ser. No. 09/918,476, Oomori et al., filed Aug. 01, 2001.

*Primary Examiner*—Russell Adams
*Assistant Examiner*—Michael Dalakis
(74) *Attorney, Agent, or Firm*—Oliff & Berridge, PLC

(57) ABSTRACT

A surface inspection apparatus determines an optimal apparatus condition setting at which a pattern layer is to be inspected based upon images of a test piece captured by an image-capturing device while irradiating illuminating light onto the surface of the test piece and varying an apparatus condition at which the images are captured. An optimal apparatus condition setting is determined by using images obtained before forming an uppermost pattern layer, an optimal apparatus condition setting is determined by using images obtained after the formation of the uppermost pattern layer and it is judged as to whether or not an image captured by the image-capturing device originates from the uppermost pattern based upon the plurality of optimal settings thus is ascertained.

26 Claims, 10 Drawing Sheets

SURFACE INSPECTION APPARATUS AND SURFACE INSPECTION METHOD

INCORPORATION BY REFERENCE

The disclosures of the following priority applications are herein incorporated by reference:
Japanese Patent Application No. 2000-277804 filed Sep. 13, 2000
Japanese Patent Application No. 2000-277805 filed Sep. 13, 2000
Japanese Patent Application No. 2000-369814 filed Dec. 5, 2000
Japanese Patent Application No. 2000-370695 filed Dec. 5, 2000

BACKGROUND OF THE INVENTION

1. Field of the Invention

The present invention relates to an apparatus and a method employed to conduct a surface inspection on a test piece such as a wafer during the process of manufacturing IC chips, liquid crystal display panels and the like.

2. Description of Related Art

Many different circuit patterns are stacked over a plurality of layers at a surface of a substrate such as a wafer to manufacture an IC chip or a liquid crystal display element panel. These circuit patterns are formed by stacking them one layer at a time on the wafer through a photolithography process or the like.

When manufacturing an IC chip, for instance, a resist is applied in a thin layer onto an oxide film formed at a surface of a wafer (substrate) and then a circuit pattern at a reticle is exposed onto the resist layer by an exposure apparatus. Next, the resist having been exposed is removed through development processing, thereby forming a pattern constituted of a resist layer achieving an identical form (or a similar reduced form) to the circuit pattern at the reticle. Subsequently, after removing the exposed oxide film through etching, the remaining resist layer is removed to form a circuit pattern constituted of the oxide film layer at the surface of the wafer. An element such as a diode is formed through doping processing or the like implemented on the circuit pattern constituted of the oxide film layer. While there is a degree of variance with regard to the manufacturing method depending upon the type of IC being manufactured, the process of forming a specific circuit pattern layer as described above is normally performed repeatedly to stack a plurality of circuit patterns over many layers on the wafer.

When circuit patterns are stacked over numerous layers on the wafer in this manner, a surface inspection is conducted to verify that no defect, abnormality or the like has occurred in the circuit pattern formed in each layer. This inspection may be implemented when, for instance, a circuit pattern constituted of the resist layer has been formed. If a surface defect, an abnormality or the like such as a deformation of the circuit pattern, inconsistency in the film thickness of the resist layer or a scar is detected during the inspection, reclaim processing is implemented for this circuit pattern layer. Namely, the resist is stripped and then a new resist layer is applied and exposed.

If a defect, an abnormality or the like occurs at any of the circuit patterns when manufacturing an IC chip or the like by stacking the circuit patterns over multiple layers on the wafer, the acceptability of the IC chip as a product is compromised. For this reason, it is crucial to conduct an inspection to detect such defects, abnormalities and the like, i.e., to conduct a wafer surface inspection.

If any defect is detected during the resist development processing stage, reclaim processing can be implemented to eliminate the defect by removing the resist and reapplying the resist layer. However, an area where a defect, an abnormality or the like is detected when a circuit pattern has been formed at an oxide layer or the like through etching cannot be reclaimed. This means that a pattern can be reclaimed by removing the resist pattern layer only as long as surface defects are detected through a surface inspection conducted at the resist development processing stage. Namely, the surface inspection conducted at the resist pattern formation stage is of especially important.

The surface inspections proposed in the related art include an inspection in which various types of inspection illuminating light are irradiated on the test piece (wafer) surface from different angles and the light reflected at the test piece is directly observed visually by the inspector as the test piece is rotated or tilted.

Such an inspection method is generally referred to as a macro inspection. When a macro inspection is implemented through visual observation by the inspector, there is a risk of inconsistency manifesting in the inspection results due to varying judgment criteria, skills and the like among individual inspectors. In addition, the onus placed on the inspector is significant. Accordingly, the possibility of automating macro inspections has been examined and various automatic macro inspection apparatuses have been proposed. For instance, there is an apparatus that performs an automatic surface inspection by irradiating inspection illuminating light onto a surface of a test piece, receiving the diffracted light from a repetitive pattern formed at the surface of the test piece with an image-capturing device to take in a diffracted image and performing image-processing on the diffracted image.

However, in the surface inspection apparatus in the related art, the optimal settings cannot be automatically selected for the apparatus conditions (the illuminating light incident angle, the tilt angle of the test piece substrate, the wavelength of the illuminating light, the position at which the light exiting the test piece and entering the image-capturing device is received and the like) when capturing a diffracted image based upon the diffracted light from the circuit pattern (repetitive pattern) on the surface of the test piece. The optimal settings in this context refer to conditions under which the direction along which the diffracted light originating from the repetitive pattern advances substantially matches the direction along which the optical axis of the light-receiving optical system that receives the diffracted light extends and, in other words, they are conditions under which a diffracted image that is good enough to enable a surface inspection is obtained.

In the surface inspection apparatus in the related art, the diffracted image of the test piece is displayed on the monitor and the inspector selects the optimal settings for the apparatus conditions by checking the diffracted image on the monitor. However, this method poses a problem in that it is not always easy for the inspector to accurately judge the optimal apparatus conditions and the inspector must have significant skills and experience.

In addition, since circuit patterns are formed over numerous layers, as explained earlier, and diffracted light originates from the individual pattern layers, there is a problem in that when a defect is detected based upon a diffracted image, it cannot be ascertained as to the specific layer from which the diffracted image has originated. For instance, a defect occurring during the process of pattern formation at a given layer may be overlooked and may be detected later during a surface inspection conducted after forming a pattern at an upper layer. In such a case, if it is erroneously judged that the defect is present at the uppermost layer, the uppermost resist pattern layer will be removed to reclaim the pattern. However, since the defect is present at the lower layer in reality, the reclaim processing described above will not solve the problem.

Thus, there is a problem with regard to the surface inspection apparatus in the related art in that it cannot be clarified as to whether or not a detected defect is present at the uppermost layer.

SUMMARY OF THE INVENTION

An object of the present invention is to provide a surface inspection apparatus and a surface inspection method that make it possible to judge as to whether or not a defect or the like detected in a surface inspection conducted on a test piece having patterns formed over numerous layers is present at the pattern at the uppermost layer.

A surface inspection apparatus according to the present invention is employed to inspect a surface of a test piece having a surface formed by stacking a plurality of pattern layers. This surface inspection apparatus comprises an illuminating optical system that irradiates illuminating light onto the surface of the test piece, an image-capturing device that captures an object image based upon diffracted light from the test piece, a condition control device that sets or changes an apparatus condition at which the object image is to be captured by the image-capturing device and a condition detection device that takes in the object image captured by the image-capturing device every time the apparatus condition is changed by the condition control device and determines an optimal condition for the apparatus condition for inspecting the pattern layers based upon the object image thus taken in. The condition detection device ascertains an optimal condition for the apparatus condition by using an image taken in before forming an uppermost pattern layer, also ascertains an optimal condition for the apparatus condition by using an image taken in after forming the uppermost pattern layer and judges as to whether or not an image captured by the image-capturing device corresponds to the uppermost pattern based upon the plurality of optimal settings thus ascertained.

The condition detection device may either ascertain the optimal condition for the apparatus condition based upon a plurality of images obtained through an image-capturing operation performed at the image-capturing device while changing the apparatus condition or ascertain the optimal condition based upon the relationship of the change in the brightness level detected in a plurality of images corresponding to the change in the apparatus condition. Alternatively, the condition detection device may detect the highest brightness levels corresponding to one of a plurality of images, ascertain the relationship of the change that the highest brightness levels manifest corresponding to the change in the apparatus condition and select as the optimal condition the apparatus condition that corresponds to the peak value among the highest brightness levels obtained by quadratically differentiating the relationship.

The apparatus condition that is changed during the inspection is constituted of at least one of; the angle of incidence at which the illuminating light from the illuminating optical system enters the test piece, the mounting angle at which the test piece is mounted, the wavelength of the illuminating light and the position at which the light exiting the test piece and entering the image-forming device is received.

The surface inspection apparatus may further comprise a defect detection device that detects a defect in a pattern formed at the test piece based upon an image having been captured by the image-capturing device at the optimal condition determined by the condition detection device to correspond to the uppermost pattern. Alternatively, the surface inspection apparatus may further comprise a storage device that stores in memory the image captured by the image-capturing device at the optimal condition determined by the condition detection device to correspond to the uppermost pattern and a defect detection device that reads out the image stored in the storage device and detects a defect at a pattern formed at the test piece based upon the image.

Furthermore, the surface inspection apparatus according to the present invention may include a storage device that stores in memory the optimal condition determined by the condition detection device to correspond to the uppermost pattern to allow the condition control device to read out the optimal condition from the storage device to set the apparatus condition based upon the optimal condition when inspecting a test piece other than the test piece used to determine the optimal condition.

In a surface inspection method according to the present invention, illuminating light is irradiated onto a surface of a test piece having a surface formed by stacking a plurality of pattern layers, an object image is captured based upon diffracted light from the test piece and a surface inspection is conducted based upon the image thus captured. In the surface inspection method, images are taken in by changing an apparatus condition during an image-capturing operation before forming an uppermost pattern layer, an optimal condition for the apparatus condition at which the pattern layer is inspected is ascertained based upon the plurality of images, images are taken in by changing the apparatus condition at which the image-capturing operation is performed after forming the uppermost pattern layer, an optimal condition for the apparatus condition at which the pattern layer is to be inspected is determined based upon the plurality of images and it is judged as to whether or not a captured image corresponds to the uppermost pattern based upon the plurality of optimal settings thus ascertained.

The optimal condition for the apparatus condition may be determined based upon a plurality of images obtained through an image-capturing operation performed by changing the apparatus condition or it may be determined based upon the relationship of the change manifested by the brightness levels detected in a plurality of images corresponding to the change in the apparatus condition. Alternatively, the highest brightness levels each corresponding to one of a plurality of images may be detected, the relationship of the change that the highest brightness levels manifest corresponding to the change in the apparatus condition may be ascertained and the apparatus condition that corresponds to a peak value among the highest brightness levels obtained by quadratically differentiating the relationship may be designated as the optimal setting.

The apparatus condition that is changed is constituted of at least one of; the angle of incidence of the illuminating light, the mounting angle at which the test piece is mounted, the wavelength of the illuminating light and the position at which the light exiting the test piece is received.

A defect at a pattern formed at the test piece may be detected based upon an image having been captured at the optimal condition determined to correspond to the uppermost pattern or may be detected based upon an image captured at the optimal condition determined to correspond to the uppermost pattern stored in memory and then read out.

In the surface inspection method according to the present invention, the optimal condition determined to correspond to the uppermost pattern may be stored in memory and the optimal condition thus stored in memory may be read out to set the apparatus condition based upon the optimal condition when inspecting a test piece other than the test piece used to determine the optimal condition.

In this surface inspection method, it is judged as to whether or not a defect is present at a plurality of pattern layers based upon images that have been captured and the pattern layer at the uppermost position undergoes reclaim processing if a defect is detected at the uppermost pattern layer among the plurality of pattern layers.

A surface inspection apparatus according to the present invention comprises an illuminating optical system that irradiates light on a surface of a test piece having a surface formed by stacking a plurality of pattern layers, a signal output device that detects diffracted light from the test piece and outputs a diffracted light signal corresponding to the quantity of the diffracted light, a condition control device that sets or changes an apparatus condition at which the diffracted light is to be detected by the signal output device and a condition detection device that determines an optimal condition for the apparatus condition at which a pattern layer is inspected based upon the diffracted light signal output by the signal output device when the condition control device changes the apparatus condition. The condition detection device determines an optimal condition for the apparatus condition by using a diffracted light signal output before forming an the uppermost pattern layer, also ascertains an optimal condition for the apparatus condition by using a diffracted light signal output after forming the uppermost pattern layer and judges as to whether or not a diffracted light signal output by the signal output device corresponds to the uppermost pattern based upon the plurality of optimal settings thus ascertained.

In a surface inspection method according to the present invention, light is irradiated by an illuminating optical system onto a surface of a test piece having a surface formed by stacking a plurality of pattern layers, a diffracted light signal corresponding to the light quantity of diffracted light from the test piece detected by a diffracted light detection unit is generated and a surface inspection is performed based upon the diffracted light signal. In this surface inspection method, diffracted light signals from the diffracted light detection unit are taken in by changing the apparatus condition at which the diffracted light detection unit performs detection before forming an uppermost pattern layer, an optimal condition for the apparatus condition at which the pattern layer is to be inspected is determined based upon the diffracted light signals, diffracted light signals from the diffracted light detection unit are taken in by changing the apparatus condition at which the diffracted light detection unit performs detection after forming the uppermost pattern layer, an optimal condition for the apparatus condition is determined based upon the diffracted light signals and it is judged as to whether or not a diffracted light signal provided by the diffracted light detection unit corresponds to the uppermost pattern based upon the plurality of optimal settings thus ascertained.

Alternatively, in a surface inspection method according to the present invention, a test piece having at least two shot areas each formed by laminating a plurality of pattern layers at a surface thereof is illuminated, an object image is captured based upon diffracted light from the test piece and a surface inspection is performed on the test piece based upon the captured object image. In this surface inspection method, a specific pattern layers in the two Or more shot areas are formed through exposure operations performed under varying exposure conditions by an exposure apparatus and other pattern layers in the two or more shot areas are formed through exposure performed under identical exposure conditions at the surface of the test piece, object images of the two or more shot areas are captured by varying the apparatus condition for capturing an object image, changes that the captured images manifest in correspondence to the change in the apparatus condition are ascertained, the changes corresponding to the two or more shot areas are compared and the apparatus condition at which the changes manifest a difference from each other is designated as the optimal condition.

A surface inspection method according to the present invention may be achieved by illuminating a test piece having shot areas each formed by laminating a plurality of pattern layers at a surface thereof, capturing an object image based upon diffracted light from the test piece and performing a surface inspection on the test piece based upon the captured object image. When forming uppermost resist layers through exposure during the shot area formation process in this surface inspection method, the resist layers are formed by varying the exposure condition at which the exposure is performed by an exposure apparatus for at least two shot areas, object images are captured by changing an apparatus condition for each of the two or more shot areas, changes that the images manifest in correspondence to the change in the apparatus condition are ascertained based upon the captured images, the changes corresponding to the two or more shot areas are compared and the apparatus condition at which the changes manifest a difference from each other is designated as an optimal condition at which the uppermost resist layers are inspected. In the surface inspection method, the uppermost resist layers are inspected at the optimal condition to allow a resist layer to be reclaimed if a defect is detected at the resist layer.

When forming the uppermost resist layer through exposure during the shot area formation process a normal pattern is formed at the resist layer in one of the two or more shot areas and a defective pattern is formed at the resist layer at the other shot area. In addition, the test piece is a semiconductor wafer utilized for testing.

DETAILED DESCRIPTION OF PREFERRED EMBODIMENTS

First Embodiment

Figure 1:
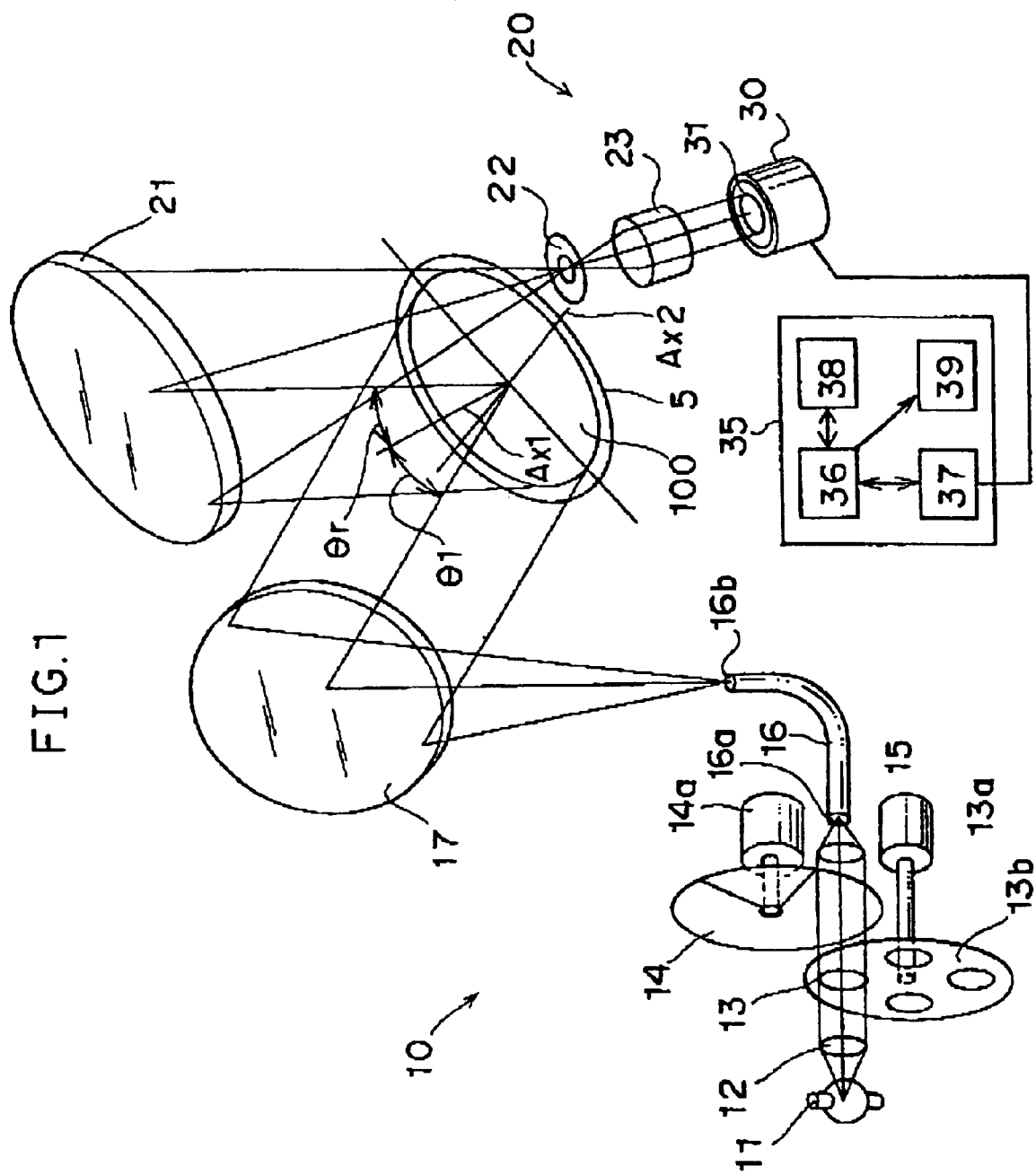
FIG. 1 is a schematic diagram illustrating the structure assumed in an embodiment of the surface inspection apparatus according to the present invention.

The following is an explanation of an embodiment of the surface inspection apparatus according to the present invention, given in reference to the drawings. FIG. 1 shows the structure assumed in an embodiment of the surface inspection apparatus according to the present invention. The surface inspection apparatus includes a holder 5 that holds a water 100 placed on it, and wafer 100 delivered by a delivery device (not shown) is placed onto the holder 5 and is securely held onto the holder 5 through vacuum holddown. The holder 5 is allowed to rotate around an axis Ax1 extending perpendicular to the surface of the securely held wafer 100 (to rotate within the wafer plane) and is also allowed to tilt around an axis Ax2 passing through the center of an illuminating system concave mirror 17 and the center of the wafer 100.

The surface inspection apparatus further includes an illuminating optical system 10 that irradiates inspection illuminating light onto the surface of the wafer 100 securely held by the holder 5, a condenser optical system 20 that condenses reflected light, diffracted light and the like from the wafer 100 irradiated by the inspection illuminating light, a CCD camera 30 (an image-capturing device) that detects an image of the surface of the wafer 100 by receiving the light condensed by the condenser optical system 20 and the like.

The illuminating optical system 10 is provided with a discharge light source 11 such as a metal halide lamp, and a collector lens 12 that condenses an illuminating light flux emitted by the discharge light source 11, the wavelength selecting filter 13 that achieves a wavelength selection by allowing the illuminating light flux having been condensed by the collector lens 12 to be transmitted, a neutral density filter 14 that performs light modulation and an input lens 15. The illuminating light flux having been transmitted through the filters 13 and 14 becomes focused through the input lens 15 and the focused illuminating light is guided into one end 16a of a fiber 16.

The wavelength selecting filter 13 is provided within a disk (turret) 13b having a switching drive mechanism 13a and the wavelength selecting filter 13 selected from various types of filters 13 is used. For instance, an interference filter that allows only light with a specific wavelength such as a g-beam (with a wavelength of 436 nm) or an i-beam (with a wavelength of 365 nm) to be transmitted, a band pass filter that allows light within a specific wavelength band to be transmitted, a sharp cut filter that allows only light having a wavelength greater than a specific wavelength to be transmitted or the like may be selected as necessary for use. The neutral density filter 14, which is constituted of a disk-shaped filter at which the quantity of transmitted light sequentially changes in correspondence to the rotational angle, is controlled by a rotation drive mechanism 14a to rotate over a specific angle to control the quantity of the transmitted light.

The illuminating optical system 10 is further provided with the illuminating system concave mirror 17, which receives a divergent light flux emitted from another end 16b of the fiber 16. The illuminating system concave mirror 17 is provided over a distance substantially matching the focal length of the illuminating system concave mirror 17 from the other end 16b of the fiber 16. As a result, the illuminating light guided into the one end 16a of the fiber 16 and diverged from the other end 16b of the fiber 16 to be irradiated on the illuminating system concave mirror 17 becomes a parallel light flux at the illuminating system concave mirror 17 and is then irradiated onto the surface of the wafer 100 held by the holder 5. The illuminating light flux irradiated onto the surface of the wafer 100 at this time achieves an angle θi relative to the axis Ax1 (vertical axis) perpendicular to the surface of the wafer 100. The illuminating light flux having been irradiated on the wafer 100 exits the wafer 100 at an angle θr relative to the axis Ax1 (vertical axis). The relationship between the incident angle θi and the exiting angle θr can be adjusted by tilting the holder 5 around the axis Ax2. Namely, the angle at which the wafer 100 is mounted can be varied by tilting the holder 5 to adjust the relationship between the incident angle θi and the exiting angle θr.

The light exiting the surface of the wafer 100 (the diffracted light in this example) is condensed at the condenser optical system 20. The condenser optical system 20 includes a condenser system concave mirror 21 facing opposite the direction extending by achieving the angle θr relative to the vertical axis Ax1, an aperture 22 provided at the position at which light is condensed at the condenser system concave mirror 21 and an image-forming lens 23 provided to the rear of the aperture 22. To the rear of the image-forming lens 23, the CCD camera 30 is provided. The lens 23 forms an image of the exiting light (nth-order diffracted light) having been condensed at the condenser system concave mirror 21 and constricted through the aperture 22 at a CCD image-capturing element (image device) 31 of the CCD camera 30. As a result, a diffracted image of the surface of the wafer 100 is formed at the CCD image-capturing element 31.

The CCD image-capturing element 31 generates an image signal through photoelectric conversion implemented on image of the surface of the wafer formed at its image receiving surface and provides the image signal thus generated to an image processing inspection device 35. The image processing inspection device 35 includes a control unit 37, a condition determining unit 38 that determines the optimal tilt angle for the wafer 100, a defect detection unit 39 that detects a defect at the wafer 100 and a memory (storage device) 36.

The control unit 37 implements control on the switching operation performed by the switching drive mechanism 13a to select a wavelength selecting filter 13, the rotation control on the neutral density filter 14 rotated by the rotation drive mechanism 14a, the control of the rotation of the holder 5 around the vertical axis Ax1, the control of the extent of the tilt of the holder 5 around the tilt axis Ax2 and the like. In addition, the control unit 37 converts the image of the wafer 100 obtained from the CCD image-capturing element 31 to a digital image with a predetermined bit-length (8-bit).

The digital image provided by the control unit 37 and the apparatus condition (the tilt angle) under which the image of the wafer 100 was obtained are stored in the memory 36. The stored digital image is output to the condition determining unit 38 when determining the optimal tilt angle for the wafer 100 and is output to the defect detection unit 39 when detecting a defect at the wafer 100. When determining the optimal tilt angle for the wafer 100, the control unit 37 takes in images of the wafer 100 by varying the tilt angle. The images of the wafer 100 at the varying tilt angles are converted to digital images as described above and are sequentially stored into the memory 36.

The condition determining unit 38 sequentially takes in the digital images of the wafer 100 stored in the memory 36, ascertains the highest brightness values (or the average brightness values) of the individual digital images and determines the optimal tilt angle $\phi s$ for the wafer 100 based upon the highest brightness values.

The defect detection unit 39 performs image processing on a digital image of the wafer 100 taken in from the memory 36, monitors the light quantity of the image and identifies a defect such as an inconsistency in the film thickness at the wafer 100, an abnormal pattern shape or a scar based upon the contrast of the image.

Since a cyclically repeated line array circuit pattern is formed at the surface of the wafer 100 constituting the test piece, the lines constituting the circuit pattern are arrayed in repetition at the surface of the wafer 100. Accordingly, with p representing the repetition pitch of the lines constituting the circuit pattern and $\lambda$ representing the wavelength of the illuminating light, the nth-order diffracted light from the wafer 100 can be condensed at the CCD camera 30 via the condenser optical system 20 by tilting the holder S at a tilt angle T formed by the surface of the wafer 100 satisfying the following equation (1). The surface is inspected to determine whether or not any defect is present based upon the image of the surface of the wafer 100 obtained at the CCD image-capturing element 31 by receiving the nth-order diffracted light in this manner.

$$\sin(\theta i - T) - \sin(\theta r + T) = n \cdot \lambda / p \quad (1)$$

In equation (1), $\theta i$ and $\theta r$ represent the values of the incident angel and the exiting angle before the tilt angle T is changed (tilt angle T=0). i.e., the initial values for the incident angle and the exiting angle. The incident angle ($\theta i - T$) and the exiting angle ($\theta r + T$) of the nth-order diffracted light after the tilt angle T is changed assume positive values along the angular direction taken toward the entry side relative to the normal line Ax1 to the surface of the wafer 100 and assume negative values along the angular direction taken toward the opposite side. The tilt angle T may assume a value of 0°, for instance, when the holder 5 is in a horizontal state, assume a positive value along the angular direction toward the entry side and a negative value along the angular direction taken toward the exiting side. The diffractive order n assumes a positive value along the angular direction taken toward the entry side relative to the 0-order light (specular reflection light) at n=0 and assumes a negative value along the angular direction taken toward the opposite side.

As described above, the image signal representing the image of the surface of the wafer 100 captured by the CCD image-capturing element 31 is provided to the image processing inspection device 35. The image processing inspection device 35 engages in pattern matching of the image of the surface of the wafer 100 obtained through the image signal provided by the CCD image-capturing element 31 and an image of the surface of an acceptable wafer product stored in memory in advance (inspection reference image) or it determines whether or not there is any difference between the characteristics of the image of the surface of the wafer 100 and the characteristics of a pre-learned inspection reference image. If a defect attributable to defocusing such as inconsistency in the film thickness, an abnormal pattern shape or a scar is present at the wafer 100 undergoing the inspection, a difference in the contrast manifesting at the defective area from the inspection reference image or a difference in the image characteristics from the inspection reference image is detected and thus, the presence of the defect is detected.

However, it cannot be ascertained as to which pattern layer among the numerous layers formed at the surface of the wafer 100 has the detected defect. Accordingly, the image processing inspection device 35 in the first embodiment performs a detection to determine whether or not the defect is present at the uppermost pattern layer. The following is a detailed explanation of the method adopted in this detection, given in reference to the flowcharts presented in FIGS. 10–12.

Determining Optimal Condition for Each Pattern Layer

Figure 2:
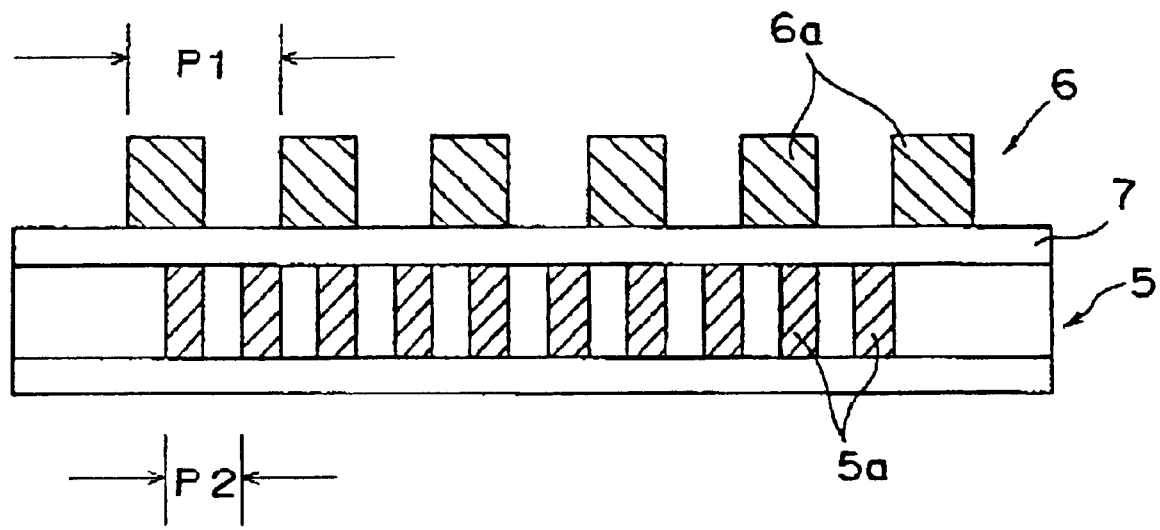
FIG. 2 is a sectional view of the pattern structure assumed in an embodiment at a surface of a wafer to undergo an inspection by the surface inspection apparatus according to the present invention.

FIG. 2 schematically illustrates pattern layers formed at the surface of the wafer 100 undergoing the inspection. FIG. 2 shows a lower layer pattern 5 constituted of a circuit pattern 5a formed at the surface of the wafer 100 through a photolithography process, an intermediate layer 7 formed on the lower layer pattern 5 and an upper layer pattern 6 constituted of a resist layer pattern 6a formed through exposure/development over the intermediate layer 7.

The lower layer pattern 5 is in a state in which a wiring circuit pattern has been formed after the completion of a circuit pattern formation step through the photolithography process. Over the lower layer pattern 5, the intermediate layer 7 constituted of a layer (e.g., an oxide layer) formed from a material used to form the next circuit pattern is provided. At the intermediate layer 7, a specific circuit pattern is formed through the photolithography process. In order to enable this circuit pattern formation, the upper layer pattern 6 constituted of the resist layer pattern 6a corresponding to the circuit pattern is formed on the intermediate layer 7. The resist layer pattern 6a is formed by applying a resist layer on the intermediate layer 7 and by exposing and developing a mask pattern at the resist layer. Thus, it is possible to perform processing for removing the upper layer pattern 6, i.e., the resist layer pattern 6a, reapplying a resist layer and reclaiming the resist layer pattern 6a in this state. However, such reclaim processing cannot be implemented for the lower layer pattern 5.

In FIG. 2, the pitch of the oxide layer pattern 5a at the lower layer pattern 5 is p2 and the pitch of the resist layer pattern 6a at the upper layer pattern 6 is p1, and thus, there is a difference between the two pitches p1 and p2. For this reason, the following point can be ascertained based upon equation (1) when conducting a surface inspection on the wafer 100 having the patterns shown in FIG. 2 formed thereupon with the surface inspection apparatus shown in FIG. 1.

When illuminating light with a wavelength λ is irradiated onto the surface of the wafer 100 with an angle of incidence (θi−T), the exiting angle (θr1+T) of the diffracted light from the upper layer pattern 6 and the exiting angle (θr2+T) of the diffracted light from the lower layer pattern 5 are expressed in the following equations (2) and (3) respectively. Since p1>p2, the relationship as expressed in expression (4) is true. Thus, (θr2+T)>(θr1+T) is also true, which means that even when the illuminating light is allowed to enter these pattern layers with angles of incidence equal to each other, the diffracted light from the individual pattern layers exit at different exiting angles.

$$\sin(\theta r1+T)=\sin(\theta i-T)-n\cdot\lambda/p1 \quad (2)$$

$$\sin(\theta r2+T)=\sin(\theta i-T)-n\cdot\lambda/p2 \quad (3)$$

$$\sin(\theta r2+T)>\sin(\theta r1+T) \quad (4)$$

The surface inspection apparatus according to the present invention relies on this fact to judge as to which layer a wafer surface image obtained based upon the diffracted light from the wafer surface corresponds to when inspecting the surface of the wafer. As a result, it becomes possible to determine as to at which layer a detected defect is present (i.e., as to whether or not the detected defect is present at the uppermost layer). In the following example, a surface inspection is first conducted as described below on an acceptable wafer product having the pattern structure shown in FIG. 2 to determine the optimal condition for the apparatus condition for each pattern layer with the condition determining unit 38.

Figure 5:
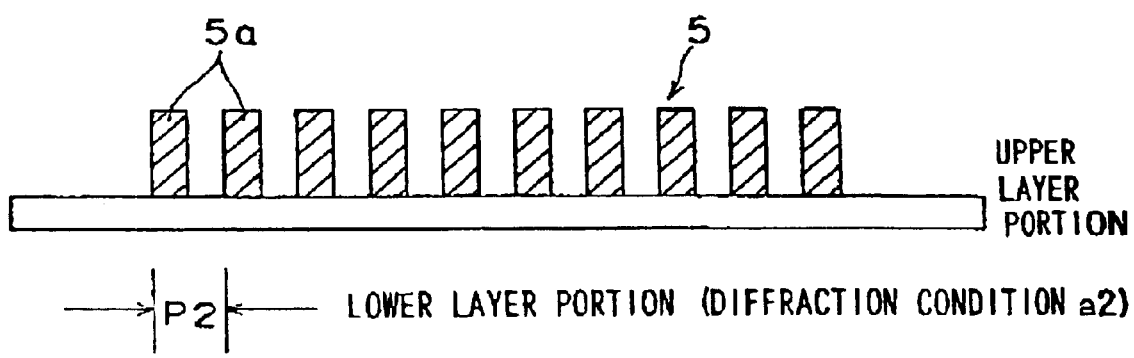
FIG. 5 presents a sectional view of the pattern structure at the surface of the wafer shown in FIG. 2 prior to the formation of the upper layer pattern.

The inspection is performed by placing and securing an acceptable wafer product having the lower layer pattern 5 shown in FIG. 5 formed thereupon onto the holder 5 and irradiating inspection illuminating light with a predetermined wavelength λ from the illuminating optical system 10 onto the surface of the wafer 100. Now, the details of this inspection are explained in reference to the flowchart in FIG. 10. The control unit 37 changes the tilt angle T of the wafer 100 by controlling the holder 5 (step S11) and takes in a two-dimensional image of the wafer surface captured by the CCD camera 30 (step S12). During this operation, a plurality of captured images corresponding to different tilt angles T and the corresponding apparatus conditions (tilt angles) are stored in the memory 36 (step S13). Images are captured by the CCD camera 30 over the entire surface of the wafer 100. More specifically, since the range over which the tilt angle varies is set so as to capture images over an incident angle range of 20°–75° with regard to the inspection illuminating light from the illuminating optical system 10, the operation to capture images of the entire surface of the wafer 100 at the various tilt angles is completed when the image intake over the full range of the tilt angle variance is completed (step S14).

Figure 11:
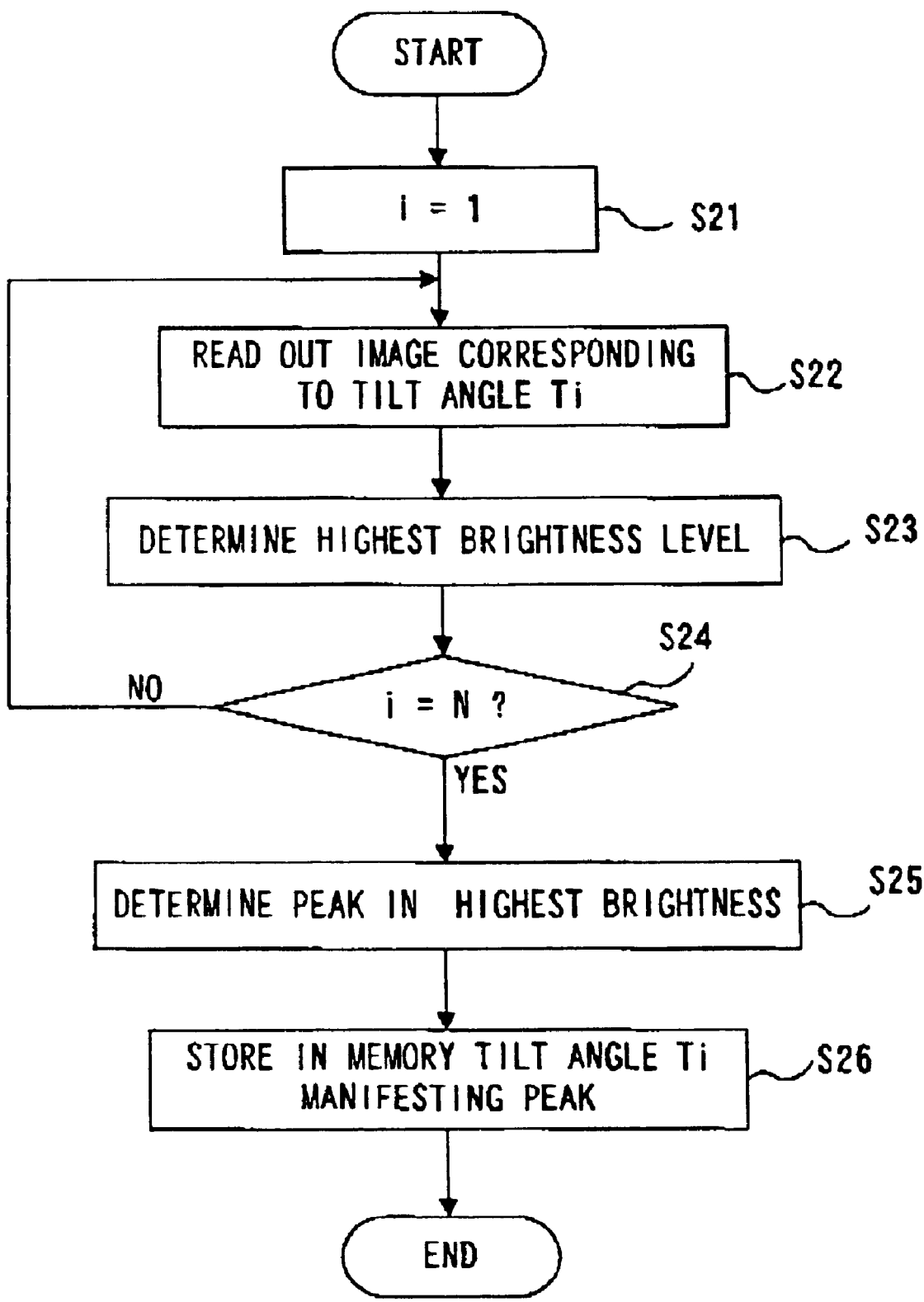
FIG. 11 is a flowchart of the processing implemented to determine the optimal condition for an image inspection.

Now, the processing implemented after the completion of the image-capturing operation for the entire surface performed at the different tilt angles is explained in reference to the flowchart in FIG. 11. The condition determining unit 38 ascertains the highest brightness value (or the average brightness value) of each image corresponding to one of the tilt angles T based upon the information of the plurality of two-dimensional images (the entire image of the wafer 100) stored in the memory 36. In more specific terms, the condition determining unit 38 reads out the image captured and stored as described above at each tilt angle Ti (i=1~N) (step S22) and ascertains the highest brightness value of each image (step S23). The processing for determining the highest brightness values of the individual image is implemented for all the images obtained through the image-capturing operation (steps S21~S24).

Figure 6:
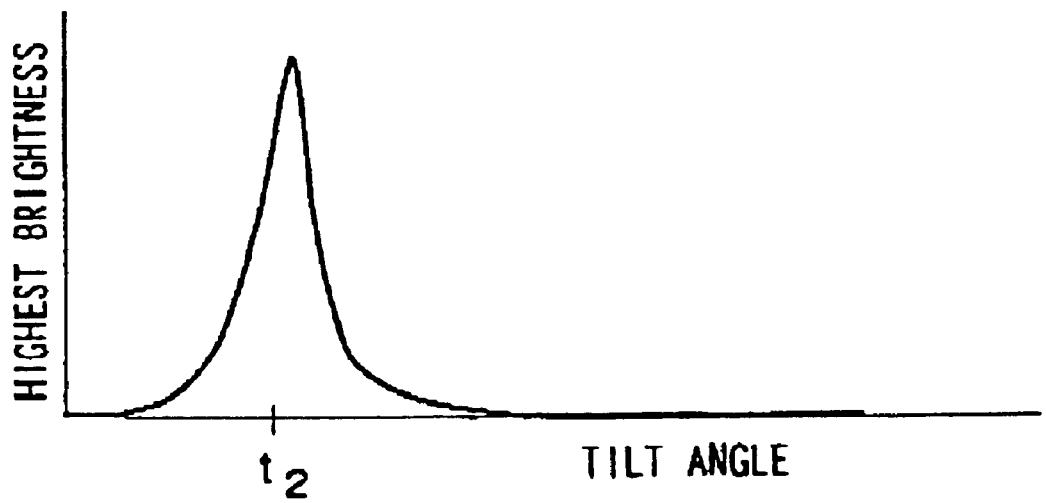
FIG. 6 presents a graph of the relationship between the tilt angle and the highest brightness obtained by inspecting the surface of the wafer shown in FIG. 5.
Figure 7:
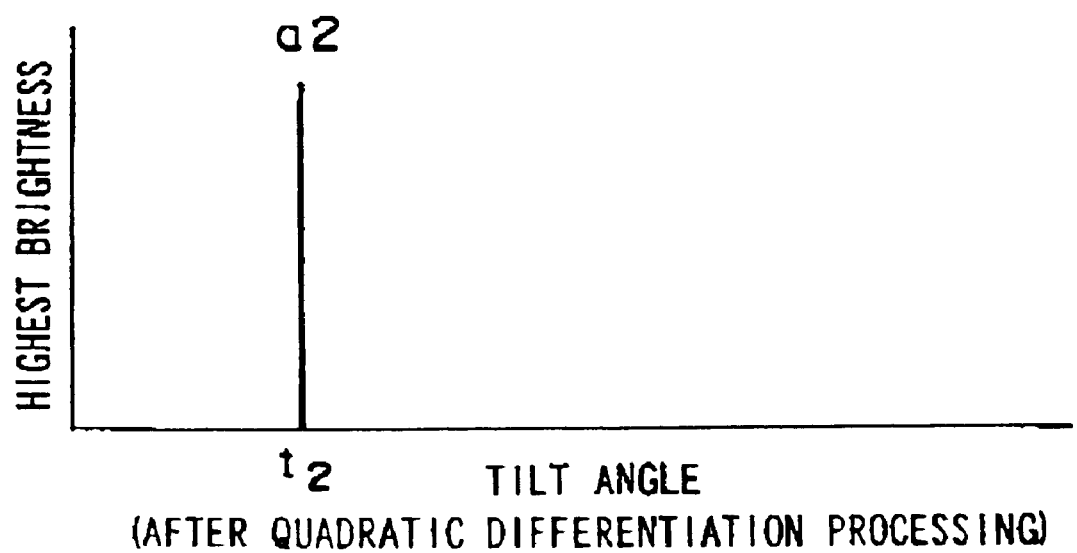
FIG. 7 presents a graph showing the results of quadratically differentiating the waveform shown in the graph in FIG. 6.

FIG. 6 shows the relationship of the highest brightness level to the tilt angle T ascertained through the processing described above. As FIG. 6 shows, the highest brightness manifests a peak when the tilt angle T is approximately at t2. The condition determining unit 38 performs processing for quadratically differentiating the waveform in FIG. 6 in order to accurately detect the peak position of the highest brightness and determines the peak position of the highest brightness (step S25). The results of the quadratic differentiation are presented in FIG. 7. As FIG. 7 shows, the highest brightness manifests the peak at the tilt angle t2. In other words, when the tilt angle is set to t2, the diffracted light from the lower layer pattern 5 enters the CCD camera 30 via the condenser optical system 20. This means that the optimal apparatus condition for inspecting the lower layer pattern 5 is T=t2. The condition determining unit 38 stores the apparatus condition, i.e., the tilt angle t2, as the optimal apparatus condition a2 for the lower layer pattern 5 in the memory 36 (step S26). The condition determining unit 38 also stores the image captured under the optimal apparatus condition a2 into the memory 36.

Next, an inspection is conducted on the acceptable wafer product having the upper layer pattern 6 formed on the lower layer pattern 5 as shown in FIG. 2.

As in the inspection of the wafer having the lower layer pattern 5 shown in FIG. 5 formed thereupon described earlier, the inspection is performed by placing and securing the wafer 100 onto the holder 5 and irradiating inspection illuminating light with the predetermined wavelength λ from the illuminating optical system 10 onto the surface of the wafer 100. The control unit 37 captures images of the entire wafer surface with the CCD camera 30 by varying the tilt angle T, takes in two-dimensional images thereof and stores the plurality of captured images corresponding to the different tilt angles T and the corresponding apparatus conditions (tilt angles) into the memory 36. This process, too, is implemented as shown in the flowchart in FIG. 10.

Figure 3:
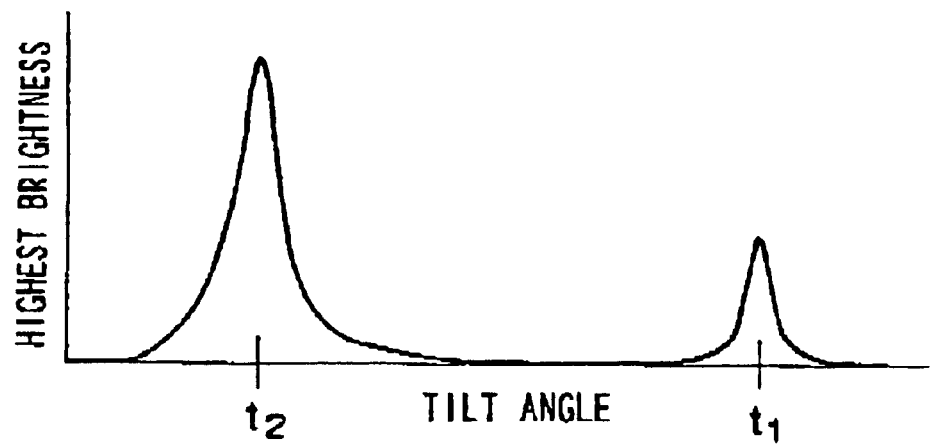
FIG. 3 presents a graph of the relationship between the tilt angle and the highest brightness obtained by inspecting the surface of the wafer shown in FIG. 2.

Next, the condition determining unit 38 ascertains the highest brightness levels (or the average brightness levels) in the individual images corresponding to the different tilt angles T based upon the information of the plurality of the two-dimensional images (the images of the entire wafer 100) stored in the memory 36. The highest brightness levels are ascertained through the procedure shown in the flowchart in FIG. 11 as described earlier. FIG. 3 shows the relationship 10 of the highest brightness to the tilt angle T as ascertained through the processing described above. As FIG. 3 indicates, the highest brightness manifests peaks when the tilt angle T is set approximately to t1 and t2.

Figure 4:
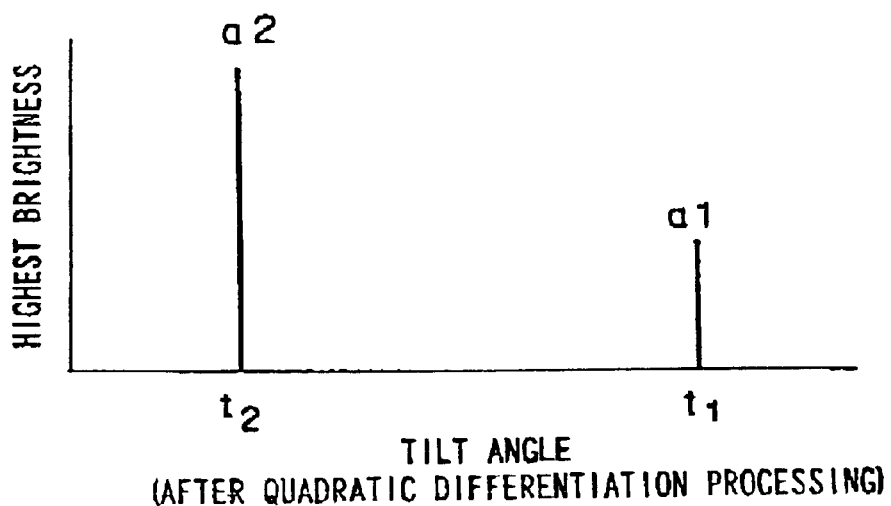
FIG. 4 presents a graph showing the results of quadratically differentiating the waveform shown in the graph in FIG. 3.

In this inspection, only the tilt angle T is changed is and images are captured with the COD camera 30 by fixing the conditions of the illuminating optical system 10 and the condenser optical system 20. Thus, the relationship between the angle of incidence (θi−T) of the illuminating light which is irradiated from the illuminating optical system 10 onto the surface of the wafer 100 and the exiting angle (θr−T) of the illuminating light changes as the tilt angle T changes. When the tilt angle T is changed to t1, the diffracted light from either the lower layer pattern 5 or the upper layer pattern 6 enters an the CCD camera 30 via the condenser optical system 20. In addition, when the tilt angle is set to t2, the diffracted light from the other pattern, i.e., the lower layer pattern 5 or the upper layer pattern 6, enters the CCD camera 30 via the condenser optical system 20. It is to be noted that the condition determining unit 38 engages in processing for quadratically differentiating the waveform in FIG. 3 and ascertains the peak positions of the highest brightness in order to accurately detect the peak positions of the highest brightness. The results of the quadratic differentiation are presented in FIG. 4. FIG. 4 indicates that the highest brightness manifests peaks when the tilt angle is set to t1 and t2.

Next, the condition determining unit 38 reads the results of the inspection conducted before the upper layer pattern 6 was formed, i.e., the inspection conducted when the lower layer pattern 5 alone had been formed as shown in FIG. 5, from the memory 36. By referencing the results of the inspection thus read, it can be ascertained that the optimal apparatus condition corresponding to the state in which the lower layer pattern 5 alone had been formed is tilt angle T=t2. This allows an assumption to be made that the peak manifesting at the tilt angle t2 among the two peaks of the highest brightness detected in the inspection performed after the formation of the upper layer pattern 6 is attributed to the diffracted light from the lower layer pattern 5, which makes it possible to determine that the peak manifesting at the tilt angle t1 corresponds to the diffracted light from the upper layer pattern 6.

As a result, it can be determined that the diffracted light from the upper layer pattern 6 enters the CCD camera 30 via the condenser optical system 20 at the tilt angle t1, which, in turn, gives the optimal apparatus condition; T=t1 for the inspection of the upper layer pattern 6. The condition determining unit 38 stores the apparatus condition; tilt angle t1, as an optimal apparatus condition a1 for the upper layer pattern 6 into the memory 36. The condition determining unit 38 also stores the image captured under the optimal apparatus condition a1 into the memory 36.

Figure 12:
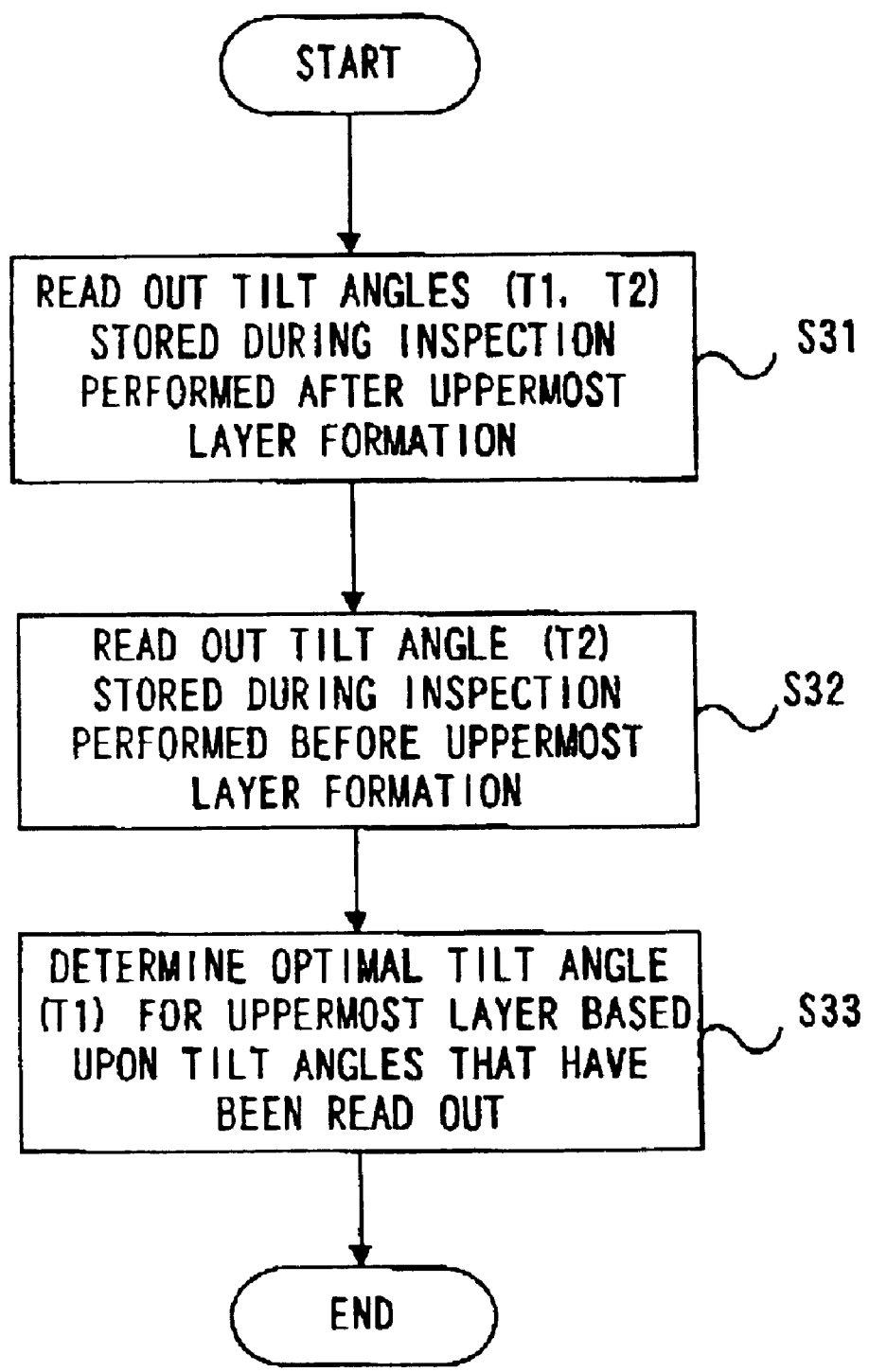
FIG. 12 is a flowchart of the processing implemented to determine the optimal condition for inspecting an uppermost pattern layer.

FIG. 12 presents a flowchart of the condition determining procedure implemented by the condition determining unit 38. The condition determining procedure is briefly explained below. In step S31. the tilt angles (t1, t2) stored during the inspection performed after the formation of the uppermost pattern layer (the upper layer pattern 6 in the first embodiment), i.e., in the inspection performed after the upper layer pattern 6 was formed on the lower layer pattern 5, as shown in FIG. 2, are read out. Next, in step S32, the tilt angle (t2) stored in the inspection performed before the formation of the uppermost pattern layer (the upper layer pattern 6 in the first embodiment), i.e., in the inspection performed with the lower layer pattern 5 alone having been formed as shown in FIG. 5, is read out from the memory 36. In step S33, by comparing the tilt angles thus read out, the optimal tilt angle (t1) for the inspection of the uppermost pattern layer (the upper layer pattern 6 in the first embodiment) is determined.

Variation

Figure 8:
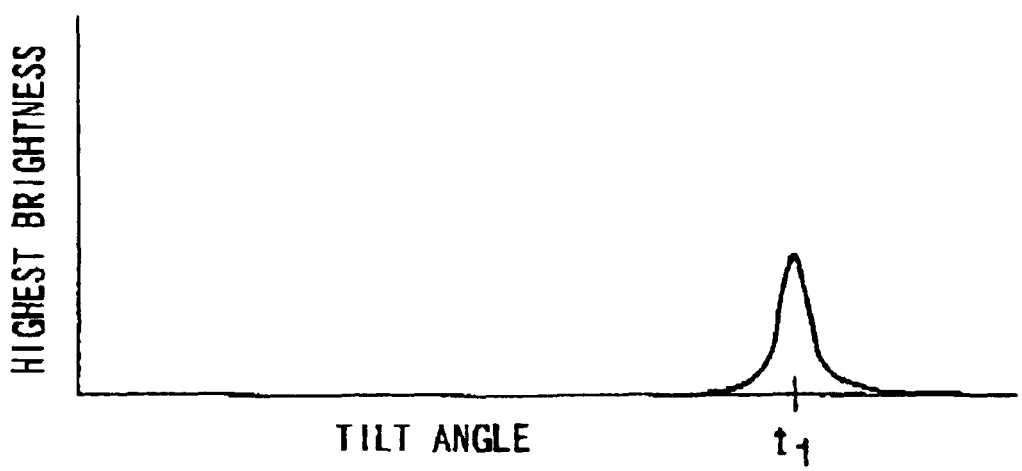
FIG. 8 presents a graph showing the difference between the relationship illustrated in FIG. 3 and the relationship illustrated in FIG. 6.

The condition determining unit 38 may instead store into the memory 36 the waveform representing the relationship of the highest brightness level to the tilt angle T shown in FIG. 3, i.e., the relationship of the highest brightness level to the tilt angle T achieved at the surface of the wafer 100 having the lower layer pattern 5 and the upper layer pattern 6 and the waveform representing the relationship of the highest brightness level to the tilt angle T manifesting when there is only the lower layer pattern 5 present at the surface shown in FIG. 6. In this case, the two waveforms are read out from the memory 36 and the difference between them is extracted. The results of the extraction are presented in FIG. 5. As shown in FIG. 8, the highest brightness level of diffracted light increases when the tilt angle is set approximately to t1.

Figure 9:
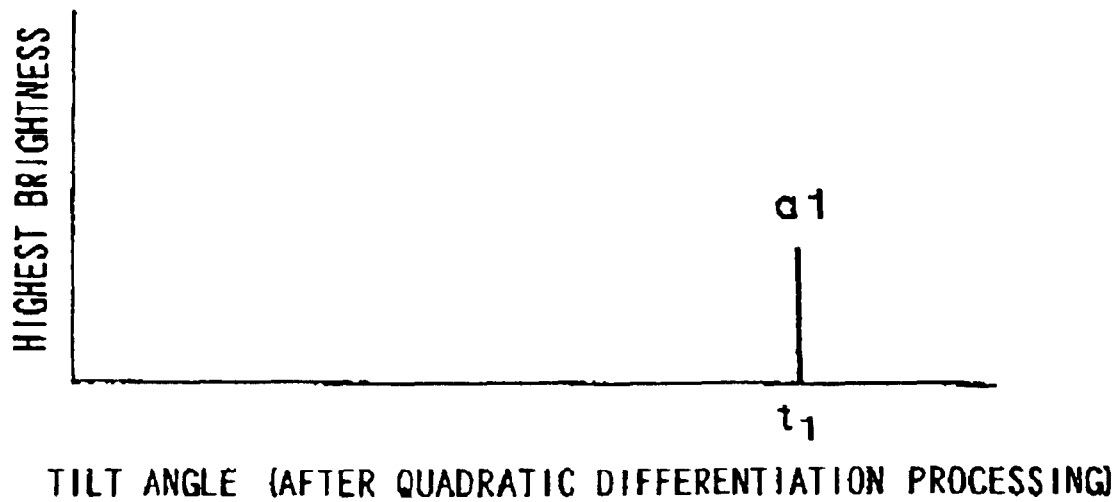
FIG. 9 presents a graph showing the results of quadratically differentiating the waveform shown in the graph in FIG. 8.

In this variation, the condition determining unit 38 further engages in quadratic differentiation of the highest brightness waveform in FIG. 8 to extract the peak position in the waveform. FIG. 9 presents the results of the quadratic differentiation. FIG. 9 indicates that a brightness peak manifests at the tilt angle t1. This means that when the tilt angle is set to t1, the diffracted light from the upper layer pattern 6 enters the CCD camera 30 via the condenser optical system 20. The condition determining unit 38 stores the tilt angle ti as an optimal apparatus condition al corresponding to the upper layer pattern 6 into the memory 36.

Through the procedure described above, the optimal apparatus condition a1 for the upper layer pattern 6 and the optimal apparatus condition a2 for the lower layer pattern 5 with respect to the acceptable wafer product 100 are stored into the memory 36, Surface Inspection Performed Under optimal Conditions A given wafer 100 (a wafer undergoing an inspection) having the pattern structure shown in FIG. 2 is inspected as described below by employing the surface inspection apparatus shown in FIG. 1.

The inspection is performed by placing and securing the given wafer 100 having the pattern structure shown in FIG. 2 onto the holder 5 and irradiating inspection illuminating light with the predetermined wavelength λ from the illuminating optical system 10 onto the surface of the wafer 100. The control unit 37 reads out the optimal apparatus condition 81 (the tilt angle t1 in this example) stored in the memory 36. The control unit 37 controls the holder 5 to set the tilt angle to t1. The control unit 37 takes in an image of the entire wafer captured by the CCD camera 30 at this setting, converts the image to a digital image and stores the digital image in the memory 36.

Next, the control unit 37 reads out the optimal apparatus condition a2 (the tilt angle t2 in this example) stored in the memory 36. The control unit 37 controls the holder 5 to set the tilt angle to t2. The control unit 37 takes in an image of the entire wafer captured by the CCD camera 30 at this setting, converts the image to a digital image and stores the digital image in the memory 36.

The defect detection unit 39 reads the digital images corresponding to the apparatus conditions a1 and a2 from the memory 36. The quantities of light of the individual images that have been read are monitored and the position at which a defect manifests at the wafer 100 is identified based upon the contrast in the images. The following is an explanation of the method adopted for identifying the position of the defect.

If a defect is detected from the image corresponding to the apparatus condition a1, the defect detection unit 39 determines that the defect is present at the upper layer pattern 6.

In this ease, reclaim processing is implemented by removing the resist layer pattern 6a constituting the upper layer pattern 6 and performing the exposure/development with a resist layer reapplied. If, on the other hand, a defect is detected from the image corresponding to the apparatus condition a2, the defect is determined to be present at the lower layer pattern 5. In such a case, since reclaim processing cannot be implemented, the IC chip containing the defect or the entire wafer itself is discarded.

As explained above, by utilizing the surface inspection apparatus in the first embodiment, it becomes possible to judge as to whether or not an image of a given test piece obtained by irradiating illuminating light onto the surface of the test piece and capturing an image of the diffracted light from the test piece with an image-capturing device originates from the uppermost pattern layer. Then, it can be determined as to whether or not a detected defect is present at the uppermost pattern layer.

Second Embodiment

Next, the second embodiment of the surface inspection apparatus according to the present invention is explained. It is to be noted that the surface inspection apparatus in the second embodiment assumes a structure identical to that of the surface inspection apparatus in FIG. 1.

Figure 13:
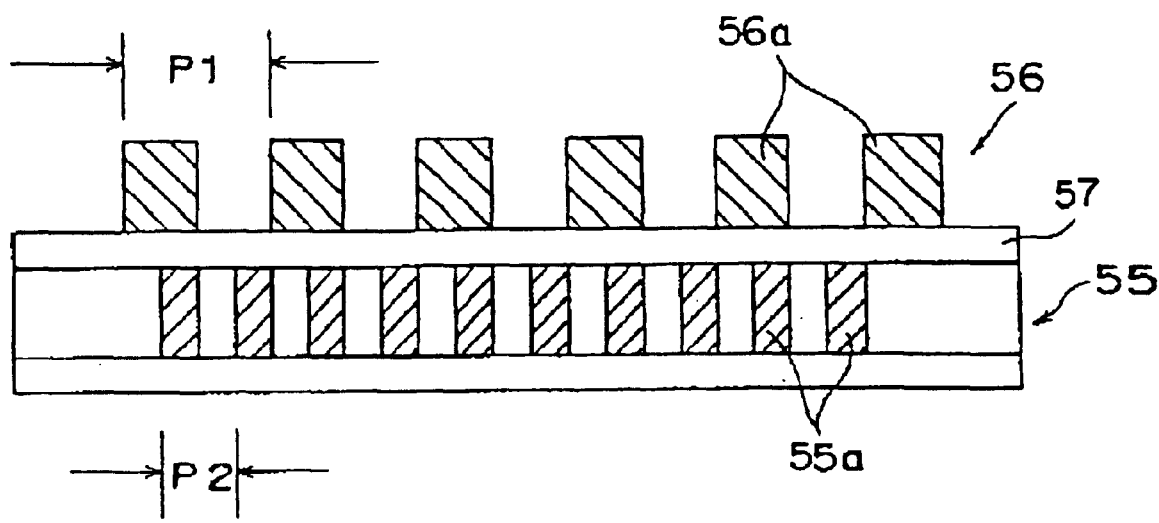
FIG. 13 is a sectional view of the pattern structure assumed in an embodiment at a surface of a wafer to undergo an inspection by the surface inspection apparatus according to the present invention.

FIG. 13 schematically shows a plurality of pattern layers formed through lamination at each shot area at the surface of the wafer. While numerous pattern layers are formed through lamination in reality, FIG. 13 schematically shows a lower layer pattern 55 constituted of a circuit pattern 55a formed through a photolithography process, an intermediate layer 57 formed on the lower layer pattern 55 and an upper layer pattern 56 constituted of a resist layer pattern 56a formed through exposure/development over the intermediate layer 57 at a given shot area at the surface of the wafer, in order to simplify the explanation.

The lower layer pattern 55 is in a state in which a wiring circuit pattern has been formed after the completion of a circuit pattern formation step in the photolithography process. Over the lower layer pattern 55, the intermediate layer 57 constituted of a layer (e.g., an oxide layer) formed from a material used to form the next circuit pattern is provided. At the intermediate layer 57, a specific circuit pattern is formed through the photolithography process. In order to enable this circuit pattern formation, the upper layer pattern 56 constituted of the resist layer pattern 56a corresponding to the circuit pattern is formed on the intermediate layer 57. The resist layer pattern 56a is formed by applying a resist layer on the intermediate layer 57 and by exposing and developing a mask pattern at the resist layer.

It is possible to perform processing for removing the upper layer pattern 56, i.e., the resist layer pattern 56a, reapplying a resist layer and reclaiming the resist layer pattern 56a in this state. However, such reclaim processing cannot be implemented for the lower layer pattern 55. It is to be noted that the pitch of the oxide layer pattern 56a at the lower layer pattern 55 is p2 and the pitch of the resist layer pattern 56a at the upper layer pattern 56 is p1, and thus, there is a difference between the two pitches p1 and p2.

Figure 14:
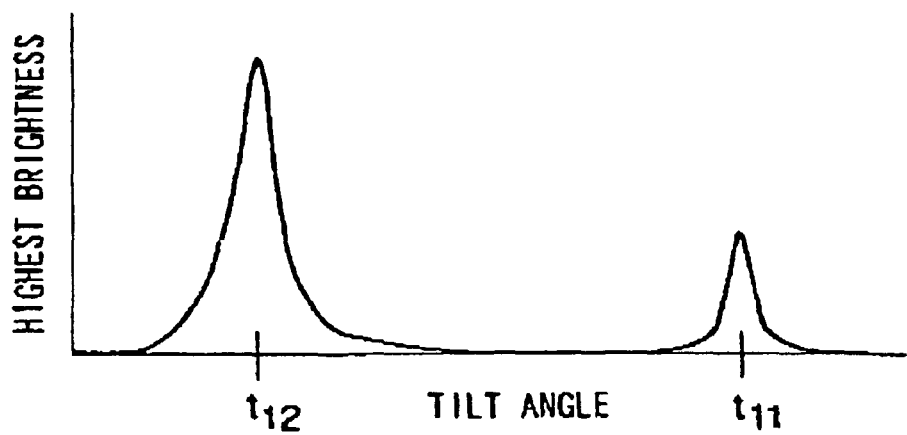
FIG. 14 presents a graph of the relationship between the tilt angle and the highest brightness obtained by inspecting the surface of the wafer shown in FIG. 13.

By performing an inspection of the wafer having the patterns shown in FIG. 13 formed thereupon with the inspection apparatus shown in FIG. 1 through the procedures described earlier (the procedures shown in the flowcharts in FIGS. 11 and 12), a peak of the highest brightness is detected at a tilt angle t11 and a tilt angle t12 as shown in FIG. 14. Namely, it is ascertained that the tilt angles t11 and t12 represent the optimal settings for inspecting the upper layer pattern 56 and the lower layer pattern 55. However, the accurate correspondence between the individual patterns and the tilt angles can not been determined at this stage.

By adopting the second embodiment, it is possible to determine which layer an image of the wafer surface obtained based upon diffracted light from the wafer surface having pattern layers with different pitches formed through lamination originates from. Namely, the optimal condition for the apparatus condition at which each pattern layer is to be inspected is selected for each of the numerous pattern layers. Thus, it becomes possible to determine as to at which layer a detected defect is present based upon the apparatus condition set when the defect is detected (as to whether or not the defect is present at the uppermost layer).

Figure 15:
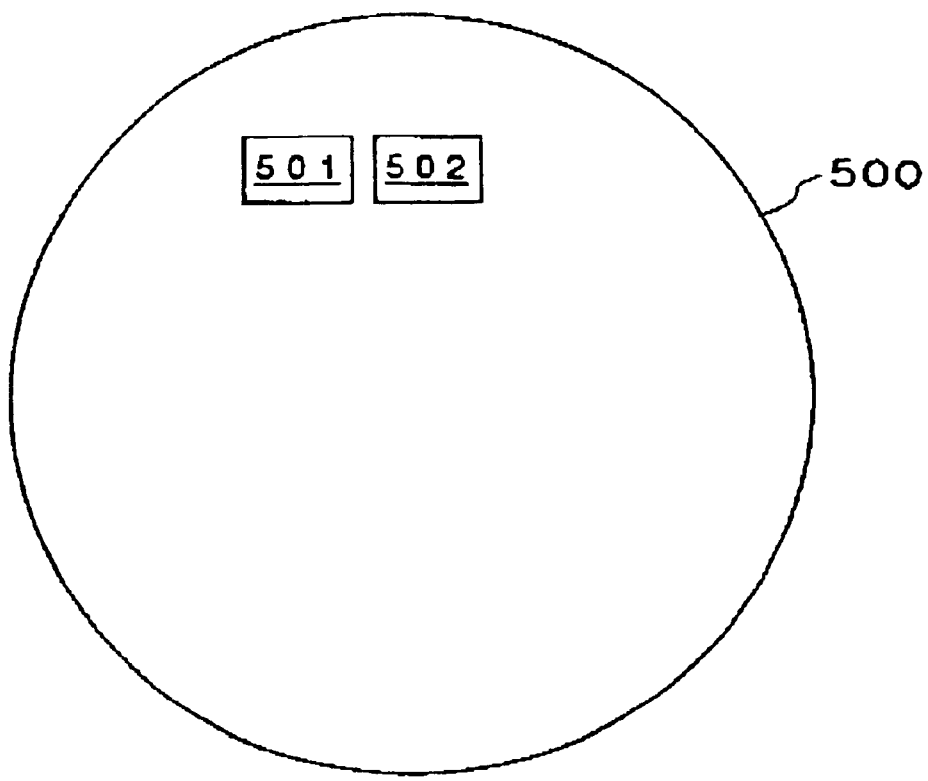
FIG. 15 is a plan view of the pattern structure assumed in an embodiment at a surface of another wafer to undergo an inspection by the surface inspection apparatus according to the present invention.

In order to allow such optimal settings for the apparatus condition to be determined, the uppermost pattern layers (the upper layer pattern 56 in FIG. 13) are formed under different exposure conditions at two specific shot areas 501 and 502 among numerous shot areas formed through exposure at the surface of a wafer 500, as shown in FIG. 15 in the second embodiment. More specifically, the upper layer pattern is formed through an exposure operation performed in a focused state for the shot area 501 and the upper layer pattern is formed through an exposure operation performed in a defocused state for the shot area 502. It is to be noted that the upper layer patterns 56 are formed in a normal manner in a focused state at the remaining shot areas. In addition, the lower layer patterns 55 are formed in the focused state in all the shot areas including the shot areas 501 and 502.

The wafer 500 is a test wafer. In other words, it is the first wafer delivered on the production line as an exposure test wafer when wafers in a single lot are to undergo exposure and inspection processes. The wafer 500 is utilized to determine various exposure conditions under which patterns are to be developed with an exposure apparatus. The exposure apparatus develops the patterns onto the wafers under the exposure conditions thus determined. For this reason, the wafer 500 is not used to form a finished semiconductor chip product.

Figure 10:
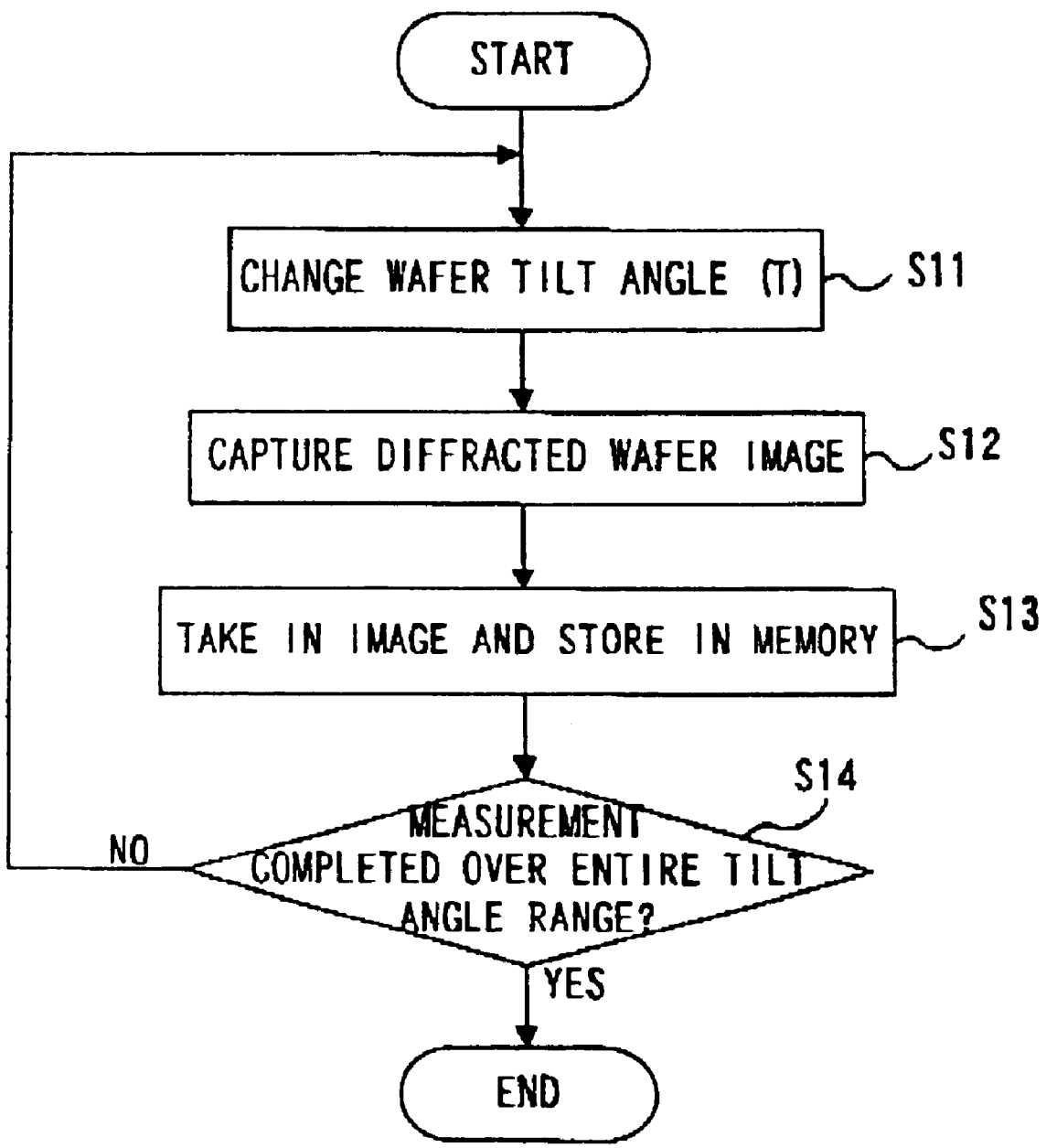
FIG. 10 is a flowchart of the image-capturing processing and the image intake processing implemented at the control unit.
Figure 16:
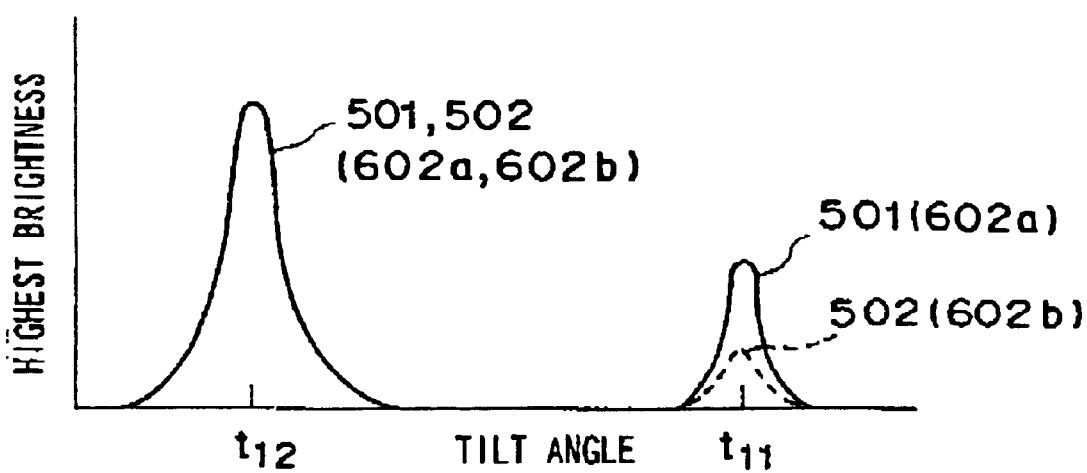
FIG. 16 presents a graph of the relationship between the tilt angle and the brightness levels at the individual shot areas obtained by inspecting the surface of the wafer shown in FIG. 15.

The inspection is performed through the procedure shown in the flowchart in FIG. 10 by placing and securing the wafer 500 onto the holder 5 of the surface inspection apparatus shown in FIG. 1 and irradiating inspection illuminating light with a predetermined wavelength λ from the illuminating optical system 10 onto the surface of the wafer 500. In addition, changes occurring in the brightness level are ascertained through the processing in the flowchart in FIG. 11 by using the images that have been obtained. However, changes in the image brightness levels in the shot area 501 and the shot area 502 are measured instead of the highest brightness levels or the average brightness levels of the overall images in this embodiment. The results of the measurement are presented in FIG. 16. While there is no difference in the brightness between the two shot areas 501 and 502 at the brightness peak detected at the tilt angle t11, the brightness level corresponding to the shot area 501 is higher than the brightness level corresponding to the shot area 502 at the brightness peak detected at the tilt angle t12.

This difference in the brightness level is attributable to the difference in the exposure conditions (focus conditions) under which the upper layer patterns 56 were formed through exposure at the shot area 501 and the shot area 502 as explained earlier. The brightness level at the shot area 501 where the upper layer pattern 56 was formed under the focused exposure condition is higher than the brightness level at the shot area 502 where the upper layer pattern 56 was formed under the defocused exposure condition. This implies that even if the optimal apparatus condition for inspecting the uppermost pattern layer is unknown, the apparatus condition (tilt angle) under which difference manifests between the changes occurring in the brightness levels at the shot areas 501 and 502 measured while changing the apparatus condition (tilt angle) may be ascertained and designated as the optimal condition for the uppermost pattern layer.

After determining the optimal condition through the procedure described above, the surface of the wafer 500 should be inspected at the optimal condition by utilizing the surface inspection apparatus shown in FIG. 1 to inspect the uppermost pattern layers (upper layer patterns 56) formed in the individual shot areas. It is to be noted that if a defect is detected in this surface inspection, the defect is judged to be present at the upper layer pattern 56. In such a case, measures such as reclaim processing can be taken by removing the resist layer pattern 56*a* constituting the upper layer pattern 56, reapplying a resist layer and performing an exposure/development operation.

As explained above, in the surface inspection apparatus achieved in the second embodiment, the optimal apparatus condition for inspecting the uppermost pattern layers which have been formed is determined by varying the exposure condition at which the uppermost pattern layers are formed through exposure at two shot areas.

The present invention is not limited to the examples presented in the embodiments described above. For instance, the surface inspection is performed under the optimal apparatus conditions stored in memory in correspondence to the upper layer pattern and the lower layer pattern in the surface inspection apparatus in the first embodiment to judge as to at which layer a detected defect is present based upon the optimal apparatus condition at which the defect is detected. Alternatively, it becomes possible to judge as to at which layer a detected defect is present by performing a surface inspection while changing the wafer tilt angle T constituting an apparatus condition and by comparing the apparatus Condition at which the defect is detected to the apparatus conditions stored in memory.

In addition, an explanation is given in reference to the surface inspection apparatus in the first embodiment on an example in which a lower layer pattern and an upper layer pattern are formed at the surface of the wafer. However, when three or more layer patterns are formed at the surface of the wafer, too, the condition determining unit 38 can determine and store in memory in advance the optimal apparatus condition for each pattern to determine at which layer a detected defect is present. In this case, too, if the defect is present at the uppermost resist layer pattern, the resist layer pattern is removed and pattern reclaim processing is performed.

In the explanation given above, a single apparatus condition, i.e., the wafer tilt angle T, alone is varied while the other apparatus conditions remain fixed to determine the tilt angle T at which the diffracted light peaks with the condition determining unit 38 based upon the brightness levels indicated by a plurality of image signals obtained through an image-capturing operation performed by the CCD camera and this tilt angle T and the other fixed conditions are set as optimal apparatus conditions. However, the optimal apparatus condition selected and stored in memory according to the present invention is not limited to the tilt angle. For instance, by varying the wavelength of the illuminating light alone and fixing all the other apparatus conditions, the condition at which the brightness of the image signal obtained through an image-capturing operation by the CCD camera peaks may be designated as the optimal apparatus condition.

Likewise, the position of the illuminating optical system may be moved to vary the angle of incidence of the illuminating light at which the illuminating light enters the wafer from the concave mirror 17. In other words, by varying the angle of incidence at which the illuminating light enters the wafer while the other conditions are fixed in the surface inspection apparatus structured as described earlier, the condition at which the brightness indicated by the image signals obtained through an image-capturing operation performed by the CCD camera peaks may be designated as the optimal apparatus condition. Furthermore, the condenser optical system 20 and the CCD camera 30 may be moved to vary the exiting angle of the light exiting the wafer surface which is then guided from the concave mirror 21 to the CCD camera 30. Namely, by varying the exiting an angle of the light exiting the wafer which is then guided to the CCD camera 30 while the other conditions are fixed and the surface inspection apparatus structured as described above, the condition at which the highest brightness level is indicated by an image signals obtained through an image-capturing operation performed by the CCD camera peaks may be designated as the optimal apparatus conditions. It goes without saying that a plurality of variable elements may be combined to determine the optimal apparatus conditions as well.

Moreover, while the tilt angles manifesting the highest brightness levels are ascertained as shown in FIG. 4 by quadratically differentiating the relationship of the highest brightness to the tilt angle T shown in FIG. 3, for instance, in the surface inspection apparatus in the first embodiment, the tilt angle T achieving the highest brightness level may be ascertained without implementing such quadratic differentiation, i.e., based upon the relationship shown in FIG. 3. However, since the relationship of the highest brightness to the tilt angle T is hardly ever as smooth as shown in FIG. 3 and is often more turbulent in reality, it is more desirable to determine the apparatus condition by comparing waveforms having undergone some type of image processing.

What is claimed is:

1. A surface inspection apparatus, comprising:

an illuminating optical system that irradiates illuminating light onto a surface of a test piece, with the surface formed by stacking a plurality of pattern layers;

an image-capturing device that captures an object image based upon diffracted light from the test piece;

a condition control device that sets or changes an apparatus condition at which the object image is to be captured by said image-capturing device; and a condition detection device that takes in the object image captured by said image-capturing device every time the apparatus condition is changed by said condition control device and determines an optimal condition for the apparatus condition for inspecting the pattern layers based upon the object image thus taken in, wherein:

said condition detection device determines an optimal condition for the apparatus condition by using an image taken in before forming an uppermost pattern layer, also determines the optimal condition for the apparatus condition by using an image taken in after forming the uppermost pattern layer and judges as to whether or not an image captured by said image-capturing device corresponds to the uppermost pattern based upon the plurality of optimal settings thus determined.

2. A surface inspection apparatus according to claim 1, wherein:

said condition detection device determines the optimal condition for the apparatus condition based upon a plurality of images obtained through an image-capturing operation performed at said image-capturing device while changing the apparatus condition.

3. A surface inspection apparatus according to claim 2, wherein:

said condition detection device detects brightness levels in a plurality of images, and determines the optimal condition based upon a change manifested by the brightness levels when the apparatus condition is changed.

4. A surface inspection apparatus according to claim 2, wherein:

said condition detection device detects highest brightness levels in a plurality of images, ascertains a change that the highest brightness levels manifest when the apparatus condition is changed and designates as the optimal condition the apparatus condition that corresponds to a peak value among the highest brightness levels obtained by quadratically differentiating the change manifested by the highest brightness levels.

5. A surface inspection apparatus according to claim 1, wherein:

the apparatus condition that is changed is at least one of; an angle of incidence at which the illuminating light from said illuminating optical system enters the test piece, a mounting angle at which the test piece is mounted, a wavelength of the illuminating light and a position at which the light exiting the test piece and entering the image-forming device is received.

6. A surface inspection apparatus according to claim 1, further comprising:

a defect detection device that detects a defect in a pattern formed at the test piece based upon an image captured by said image-capturing device at the optimal condition determined by said condition detection device to correspond to the uppermost pattern.

7. A surface inspection apparatus according to claim 1, further comprising:

a storage device that stores in memory an image captured by said image-capturing device under the optimal condition determined by said condition detection device to correspond to the uppermost pattern; and a defect detection device that reads out the image stored in said storage device and detects a defect at a pattern formed at the test piece based upon the image thus read.

8. A surface inspection apparatus according to claim 1, further comprising:

a storage device that stores in memory an optimal condition determined by said condition detection device to correspond to the uppermost pattern, wherein:
said condition control device reads out the optimal condition from said storage device to select the apparatus condition based upon the optimal condition when inspecting a test piece other than the test piece used to determine the optimal condition.

9. A surface inspection method for performing a surface inspection based upon an image obtained by irradiating illuminating light onto a surface of a test piece with the surface formed by stacking a plurality of pattern layers and capturing an object image based upon diffracted light from the test piece, wherein:

images are taken in by changing an apparatus condition during an image-capturing operation before forming an uppermost pattern layer and an optimal condition for the apparatus condition for inspecting a pattern layer is determined based upon the plurality of images;

images are taken in by changing the apparatus condition at which said image-capturing operation is performed after forming the uppermost pattern layer and an optimal condition for the apparatus condition for inspecting the pattern layer is determined based upon the plurality of images; and it is judged as to whether or not a captured image corresponds to the uppermost pattern based upon the plurality of optimal settings.

10. A surface inspection method according to claim 9, wherein:

the optimal condition for the apparatus condition is determined based upon a plurality of images obtained through an image-capturing operation performed while changing the apparatus condition.

11. A surface inspection method according to claim 10, wherein:

brightness levels in a plurality of images are detected and the optimal condition is determined based upon a change manifested by the brightness levels as the apparatus condition is changed.

12. A surface inspection method according to claim 10, wherein:

the highest brightness levels in a plurality of images are detected, a change manifested by the highest brightness levels as the apparatus condition is changed is ascertained and the apparatus condition corresponding to a peak value among the brightness levels obtained by quadratically differentiating the change manifested by the highest brightness levels is designated as the optimal condition.

13. A surface inspection method according to claim 9, wherein:

the apparatus condition that is changed is at least one of; an angle of incidence of the illuminating light, a mounting angle at which the test piece is mounted, a wavelength of the illuminating light and a position at which the light exiting the test piece is received.

14. A surface inspection method according to claim 9, wherein:

a defect at a pattern formed at the test piece is detected based upon an image captured at the optimal condition determined to correspond to the uppermost pattern.

15. A surface inspection method according to claim 9, wherein:

an image captured at the optimal condition determined to correspond to the uppermost pattern is stored in memory;

the image that has been stored is read out and a defect at a pattern formed at the test piece is detected based upon the image that has been read out.

16. A surface inspection method according to claim 9, wherein:

the optimal condition determined to correspond to the uppermost pattern is stored in memory; and the optimal condition that has been stored in memory is read out and an apparatus condition is selected based upon the optimal condition when inspecting a test piece other than the test piece used to determine the optimal condition.

17. A surface inspection method according to claim 9, wherein:

it is judged as to whether or not a defect is present at a plurality of pattern layers based upon images that have been captured; and the uppermost pattern layer undergoes reclaim processing if a defect is detected at the uppermost pattern layer among the plurality of pattern layers.

18. A surface inspection apparatus, comprising:

an illuminating optical system that irradiates light on a surface of a test piece with the surface of the test piece formed by stacking a plurality of pattern layers;

a signal output device that detects diffracted light from the test piece and outputs a diffracted light signal corresponding to a quantity of the diffracted light;

a condition control device that sets or changes an apparatus condition at which the diffracted light is detected by said signal output device; and a condition detection device that determines an optimal condition for the apparatus condition for inspecting the pattern layers based upon a diffracted light signal output by said signal output device when said condition control device changes the apparatus condition, wherein:

said condition detection device determines an optimal condition for the apparatus condition by using a diffracted light signal output before forming an uppermost pattern layer, also determines an optimal condition for the apparatus condition by using a diffracted light signal output after forming the uppermost pattern layer and judges as to whether or not a diffracted light signal output by said signal output device corresponds to the uppermost pattern based upon the plurality of optimal settings thus determined.

19. A surface inspection method for performing a surface inspection by performing a surface inspection based upon a diffracted light signal by irradiating light with an illuminating optical system onto a surface of a test piece with the surface formed by stacking a plurality of pattern layers and generating the diffracted light signal corresponding to a quantity of diffracted light from the test piece detected by a diffracted light detection unit, wherein:

diffracted light signals from said diffracted light detection unit are taken in by changing the apparatus condition at which said diffracted light detection unit performs detection before forming an uppermost pattern layer, and an optimal condition for the apparatus condition for inspecting the pattern layer is determined based upon the diffracted light signals;

diffracted light signals from said diffracted light detection unit are taken in by changing the apparatus condition at which said diffracted light detection unit performs detection after forming the uppermost pattern layer, and an optimal condition for the apparatus condition is determined based upon the diffracted light signals; and it is judged as to whether or not a diffracted light signal provided by said diffracted light detection unit corresponds to the uppermost pattern based upon the plurality of optimal settings.

20. A surface inspection method for performing a surface inspection on a test piece having at least two shot areas each formed by laminating a plurality of pattern layers at a surface thereof based upon an object image captured from diffracted light from the test piece by illuminating the test piece, wherein:

specific pattern layers in the two or more shot areas are formed through exposure operations performed under varying exposure conditions by an exposure apparatus and other pattern layers in the two or more shot areas are formed through exposure performed under identical exposure conditions;

object images of the two or more shot areas are captured by varying the apparatus condition for object image capturing and changes that the images manifest in correspondence to the change in the apparatus condition are ascertained based upon the captured images; and the changes that the images manifest corresponding to the two or more shot areas are compared and the apparatus condition at which the changes manifest a difference from each other is designated as the optimal condition.

21. A surface inspection method for performing a surface inspection on a test piece having shot areas each formed by laminating a plurality of pattern layers at a surface thereof based upon an object image captured from diffracted light from the test piece by illuminating the test piece, wherein:

when forming uppermost resist layers through exposure during the shot area formation process, the resist layers are formed through exposure operations performed under varying exposure conditions by an exposure apparatus over at least two shot areas;

object images are captured by changing the apparatus condition for each of the two or more shot areas and changes that the images manifest in correspondence to the change in the apparatus condition are ascertained based upon the captured images; and the changes corresponding to the two or more shot areas are compared and the apparatus condition at which the changes manifest a difference from each other is designated as an optimal condition for inspecting the uppermost resist layer.

22. A surface inspection method according to claim 21, wherein:

the uppermost resist layer is inspected at the optimal condition and the resist layer undergoes reclaim processing if a defect is detected at the resist layer.

23. A surface inspection method according to claim 20, wherein:

a normal pattern is formed at the uppermost resist layer in one of the two or more shot areas and a defective pattern is formed at the uppermost resist layer at the other shot area when forming the shot areas through exposure.

24. A surface inspection method according to claim 20, wherein:

the test piece is a semiconductor wafer utilized for testing.

25. A surface inspection method according to claim 21, wherein:

a normal pattern is formed at the uppermost resist layer in one of the two or more shot areas and a defective pattern is formed at the uppermost resist layer at the other shot area when forming the shot areas through exposure.

26. A surface inspection method according to claim 21, wherein:

the test piece is a semiconductor wafer utilized for testing.

* * * * *